US009551651B2

(12) United States Patent
Hegeman et al.

(10) Patent No.: US 9,551,651 B2
(45) Date of Patent: Jan. 24, 2017

(54) HANDHELD MOISTURE SENSOR DEVICE (71) Applicants: Digi-Star, LLC, Fort Atkinson, WI (US); Rock River Laboratory, Inc., Watertown, WI (US)

(72) Inventors: Daniel J. Hegeman, Whitewater, WI (US); Samuel R. Vorpahl, Fort Atkinson, WI (US); Donald W. Meyer, Ixonia, WI (US); Crystal A. Dixon, Belleville, IL (US)

(73) Assignees: Digi-Star, LLC, Fort Atkinson, WI (US); Rock River Laboratory, Inc., Watertown, WI (US)

( * ) Notice: Subject to any disclaimer, the term of this patent is extended or adjusted under 35 U.S.C. 154(b) by 5 days.

(21) Appl. No.: 14/309,415

(22) Filed: Jun. 19, 2014

(65) Prior Publication Data

US 2014/0374598 A1    Dec. 25, 2014

Related U.S. Application Data (60) Provisional application No. 61/836,988, filed on Jun. 19, 2013.

(51) Int. Cl.
*G01N 21/27* (2006.01)
*G01N 21/25* (2006.01)
(Continued)

(52) U.S. Cl.
CPC ............ *G01N 21/27* (2013.01); *G01J 3/0264* (2013.01); *G01J 3/0291* (2013.01); *G01J 3/108* (2013.01);
(Continued)

(58) Field of Classification Search
CPC ..... G01N 21/335; G01N 21/27; G01N 21/255
See application file for complete search history.

(56) References Cited

U.S. PATENT DOCUMENTS 6,052,187 A    4/2000 Krishnan et al.
6,100,526 A *  8/2000 Mayes ................ A01D 41/127
                                              250/339.11
(Continued)

OTHER PUBLICATIONS

Malinen et al., LED-based NIR spectrometer module for hand-held and process analyser applications, 1998, Sensors and Actuators, vol. 51, pp. 220-224.*

(Continued)

*Primary Examiner* — Christine Sung
(74) *Attorney, Agent, or Firm* — Chiesa Shahinian & Giantomasi PC (57) ABSTRACT A handheld moisture sensing device for use in determining the moisture content of biological material, such as animal feed. Adapted to be pressed against biological material to be analyzed, the device includes a sensor assembly, including a housing with an end structure including a grate adapted to engage the material to be examined, a near infrared (NIR) LED, an NIR light sensor, a glass mounted in the housing adjacent the light source so that light from the light source passes through the glass, a glass heater positioned adjacent the glass for heating the glass, a lens mounted in the housing adjacent the NIR sensor so that the NIR light reflected off the biological material passes through the glass and is focused by the lens onto the NIR sensor, and a controller connected to the NIR sensor and receiving a signal related to the reflected NIR light received by the NIR sensor.

13 Claims, 9 Drawing Sheets

(51) Int. Cl.
*G01N 33/02* (2006.01)
*G01N 33/00* (2006.01)
*G01N 21/3554* (2014.01)
*G01N 21/359* (2014.01)
*G01J 3/02* (2006.01)
*G01J 3/10* (2006.01)
*G01N 21/35* (2014.01)

(52) U.S. Cl.
CPC .......... *G01N 21/255* (2013.01); *G01N 21/359* (2013.01); *G01N 21/3554* (2013.01); *G01N 33/0098* (2013.01); *G01N 33/02* (2013.01); *G01J 2003/104* (2013.01); *G01N 21/278* (2013.01); *G01N 21/35* (2013.01); *G01N 2201/0221* (2013.01); *G01N 2201/062* (2013.01)

(56) References Cited

U.S. PATENT DOCUMENTS

| | | | |
|---|---|---|---|
| 7,428,042 B2 | 9/2008 | Ghiraldi | |
| 7,791,027 B2* | 9/2010 | McAllister | G01J 3/02 |
| | | | 250/339.07 |
| 8,108,170 B1 | 1/2012 | Shenk et al. | |
| 8,146,624 B2 | 4/2012 | Ghiraldi | |
| 8,548,764 B1 | 10/2013 | Shenk et al. | |
| 8,608,368 B2 | 12/2013 | Bresciani | |
| 8,651,730 B2 | 2/2014 | Barbi | |
| 2002/0026937 A1 | 3/2002 | Mault | |
| 2003/0025513 A1* | 2/2003 | Falbo | G01N 33/10 |
| | | | 324/664 |
| 2005/0074146 A1* | 4/2005 | Jones | G01N 15/1475 |
| | | | 382/110 |
| 2008/0239293 A1 | 10/2008 | Fuchigami et al. | |
| 2008/0291455 A1 | 11/2008 | Holland | |
| 2009/0250595 A1* | 10/2009 | Kalitsis | G01N 21/3563 |
| | | | 250/208.2 |
| 2010/0032572 A1 | 2/2010 | Shelley et al. | |
| 2010/0078564 A1 | 4/2010 | McAllister et al. | |
| 2011/0054864 A1 | 3/2011 | Lundstedt et al. | |
| 2012/0056093 A1* | 3/2012 | Poteet | G01J 3/02 |
| | | | 250/362 |
| 2012/0112072 A1* | 5/2012 | Jones | G01N 21/359 |
| | | | 250/339.07 |
| 2012/0194800 A1 | 8/2012 | Debreczeny | |
| 2013/0258341 A1* | 10/2013 | Day | G01J 3/0291 |
| | | | 356/402 |

OTHER PUBLICATIONS

Sundaram et al., Sensing of Moisture Content of In-Shell Peanuts by NIR Reflectance Spectroscopy, Mar. 2012, Journal of Sensor Technology, vol. 2, pp. 1-7.*

* cited by examiner

HANDHELD MOISTURE SENSOR DEVICE

CROSS REFERENCE TO RELATED APPLICATION

This application claims the benefit of U.S. Provisional Patent Application Ser. No. 61/836,988, filed Jun. 19, 2013, the disclosure of which is hereby incorporated by reference herein in its entirety for all purposes.

FIELD OF THE INVENTION

The present invention relates generally to the field of biological matter management. More particularly, the present invention relates to apparatuses and systems for sensing moisture content in biological matter, such as animal feed.

BACKGROUND

A livestock manager needs to know the level of moisture in feed so that the manager knows the true amount of nutrition being fed. That is, particularly relating to the feeding of forages to livestock, feeding cannot be done simply on the basis of the weight of the feed being fed. Moisture content has a substantial impact on the weight of feed, but no impact on the nutrition of the feed. The amount of feed to mix and feed to livestock is determined by the DMI (Dry Matter Intake) of the feed. In addition, farm managers would like to know the DMI of all field harvested commodities to determine total tonnage of harvest.

Measuring the moisture content of forages with a near infrared (NIR) spectrometer is not new, but there are many disadvantages to the current methods and apparatus being used. Most livestock managers today use one of the three methods below for measuring the moisture content.

A. Weighing the forage material wet, then drying the material and weighing it again. This is the method employed in the use of a Koster Tester. Based on the difference in weight, one can calculate the percentage of moisture that was in the original forage material. This process typically takes 30-45 minutes, and the reliability is based upon the ability of the operator to take a representative sample of the forage, as opposed to the dried out material at the top or exposed area of a collection of forage. In addition, volatiles other than water can be driven off during the drying process, resulting in inaccurate water moisture results.

B. Using a spectrum analyzer for moisture and other constituents, such as proteins, starches, etc. The disadvantage here is that a spectrum analyzer typically costs in the range of $10,000-$20,000 or more, and the operator may not be interested in those other constituents.

C. Sending samples to a laboratory. This method can be lower in cost, but is slow, normally taking days to get results.

Clearly, a better method and apparatus are needed to properly sense the moisture in animal feeds, so that a livestock manager can quickly (in seconds), easily, inexpensively and accurately determine the dry matter intake of the feed being fed to the livestock.

SUMMARY OF THE INVENTION

The invention provides a handheld moisture sensing device for use in determining the moisture content of biological material, such as animal feed. The device is adapted to be pressed against biological material to be analyzed. The device includes a sensor assembly, including a housing with an end structure including a grate adapted to engage the material to be examined. A near infrared LED is mounted in the housing. A near infrared light sensor is also mounted in the housing, and is positioned to receive near infrared light from the near infrared LED, reflected off of the material. The sensor is located along a central axis of the spectroscope, and the LED is located spaced apart from the sensor. A glass is mounted in the housing in front of the light source so that light from the light source passes through the glass. The glass is spaced apart from the grate, with a lens focusing the energy to the near infrared light sensor. A glass heater is positioned near the glass for providing heat, the glass heater including a temperature sensor so that the heater is activated in response to the glass temperature being lower than a predetermined value. A lens is mounted in the housing adjacent the near infrared sensor so that the near infrared light reflected off the biological material passes through the glass and is focused by the lens onto the near infrared sensor. A controller is connected to the near infrared sensor and receives a signal related to the reflected near infrared light received by the near infrared sensor. The controller includes a user input for selecting the material to be scanned, and determines, based on the reading of reflected near infrared light, the amount of amount of wet material present, from which the dry matter is calculated.

It will be understood by those skilled in the art that one or more aspects of this invention can meet certain objectives, while one or more other aspects can lead to certain other objectives. Other objects, features, benefits and advantages of the present invention will be apparent in this summary and descriptions of the disclosed embodiment, and will be readily apparent to those skilled in the art. Such objects, features, benefits and advantages will be apparent from the above as taken in conjunction with the accompanying figures and all reasonable inferences to be drawn therefrom.

DETAILED DESCRIPTION

Figure 1:
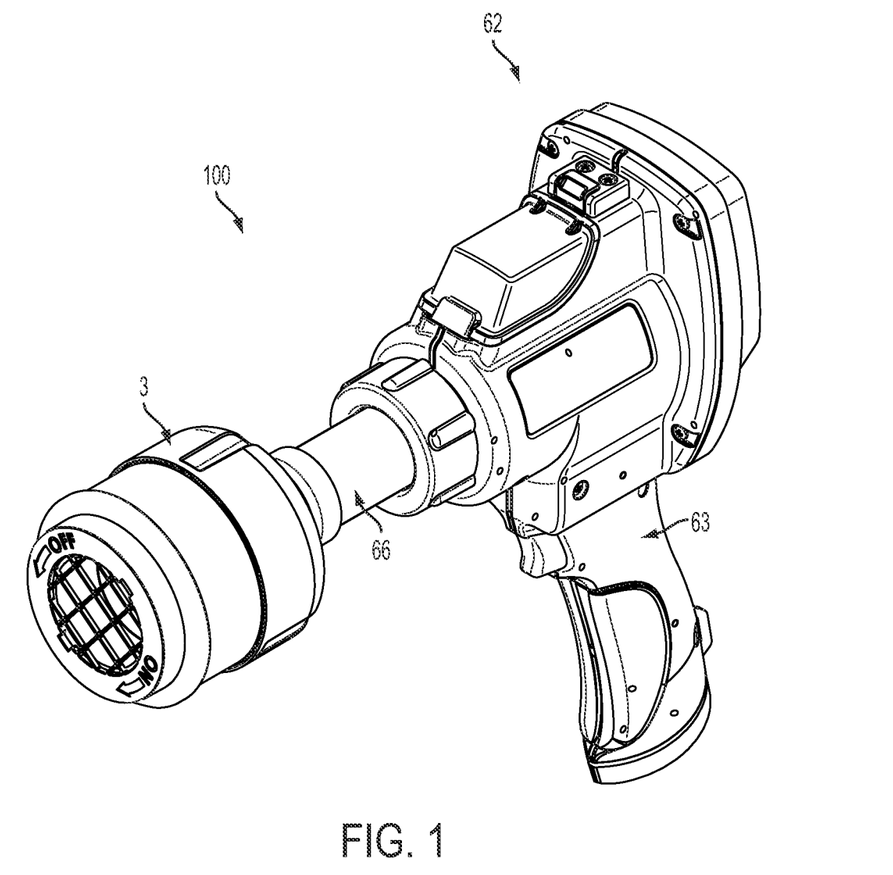
FIG. 1 is a perspective view of a handheld moisture sensor device constructed according to a preferred embodiment of the invention.
Figure 2:
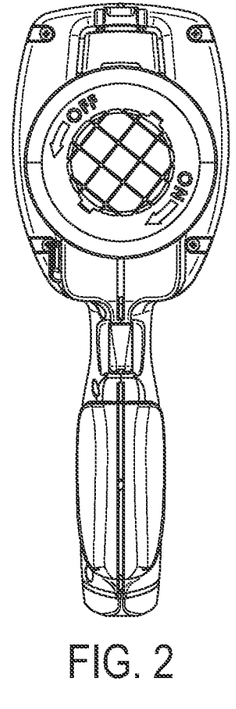
FIG. 2 is a front view of the moisture sensor device of FIG. 1.
Figure 3:
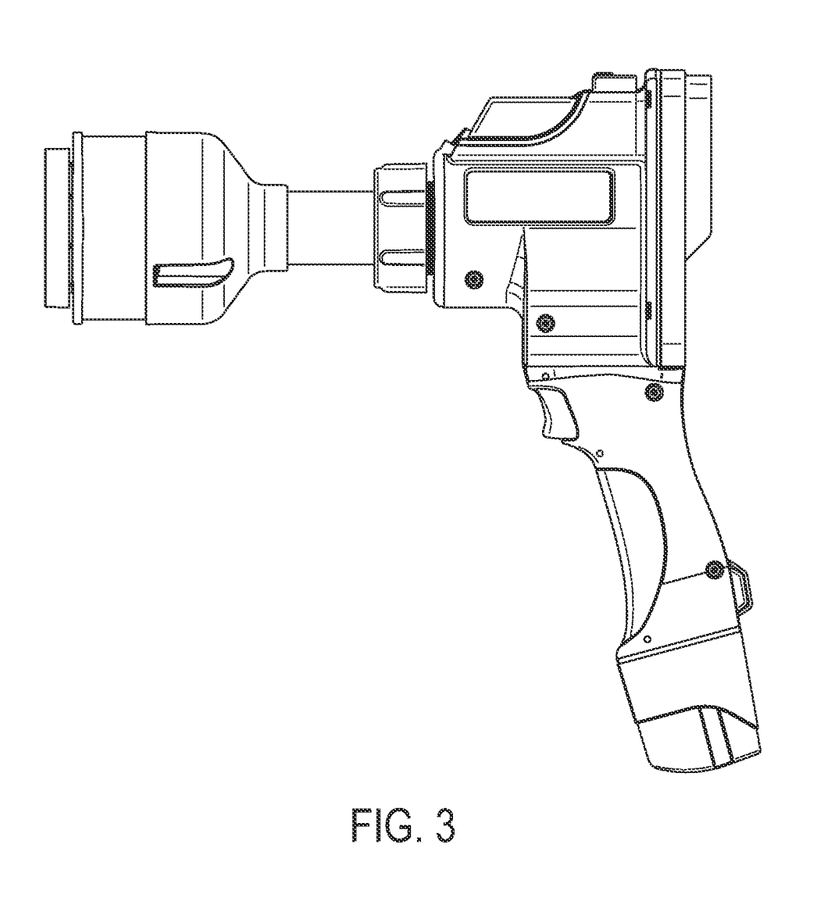
FIG. 3 is a side view of the moisture sensor device of FIG. 1.
Figure 4:
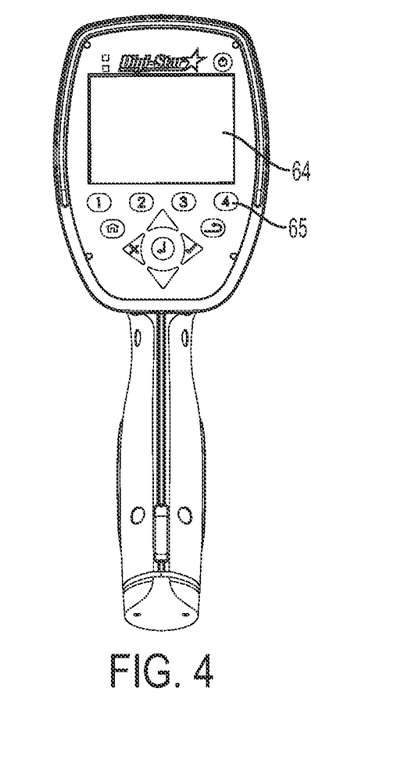
FIG. 4 is a rear view of the moisture sensor device of FIG. 1.
Figure 5:
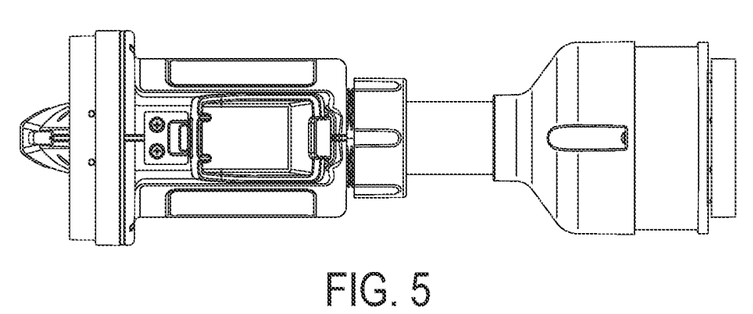
FIG. 5 is a top view of the moisture sensor device of FIG. 1.

Shown in FIG. 1 is a preferred embodiment of a handheld moisture sensor device or near infrared spectroscope 100 for detecting the water component of various biological materials, such as animal feed, and calculating the dry component. The sensor device 100 is adapted to be pressed against the material to be analyzed. In the embodiment shown, the sensor device 100 includes a head unit 62, having a hand holdable grip or handle 63, a display 64 (see FIG. 4) and a number of controls 65, which may include buttons, dials, and/or other controls. The sensor device 100 also includes a wand 66, connected at one end to the head unit 62. The other end of the wand 66 is connected to a sensor assembly or probe 3. The wand 66 can be various lengths, depending on the sensor's intended use, for example, from three inches or less to three feet and beyond.

Figure 6:
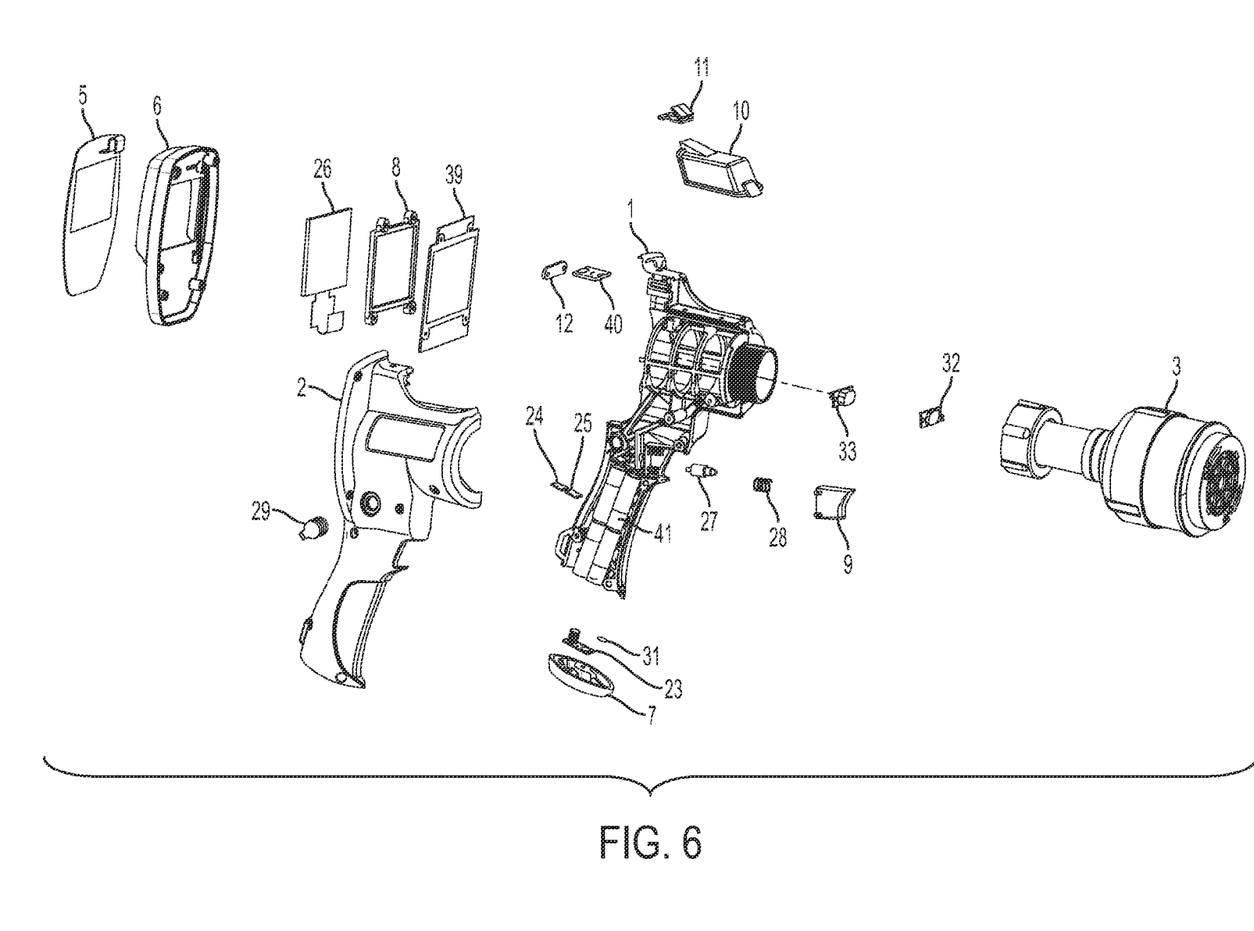
FIG. 6 is an exploded isometric view of the handheld moisture sensor device shown in FIG. 1.

As shown in the exploded isometric drawing in FIG. 6, the head unit 62 includes a main processor/controller 39, connected to the display 64 and the controls 65.

More particularly, the various elements of the device 100 is detailed in the following list.

REFERENCE NUMERAL DESCRIPTION

1 left handle assembly
2 right handle assembly
3 probe assembly
4 frame
5 switch panel overlay
6 back plate
7 battery door
8 display mount

REFERENCE NUMERAL DESCRIPTION

11 USB door clip
12 USB locking tab
23 spring battery terminal
24 battery terminal
25 spring coil battery terminal
26 LCD display
27 trigger switch
28 trigger spring
29 power jack connector cap
30 door lanyard
31 vent patch
32 9-pin D-sub female connector
33 9-pin D-sub male connector
40 USB PCB assembly Mounted within the handle 63 is the power source, shown here as dry cell batteries 41, which may be single use or rechargeable, or just as well a unitary battery pack with a cable and plug connection, with rechargeable or single use cells. The head 62 also has physical and electrical connectors permitting removable connection to the wand 66. Several different lengths of wand, both short and long, can be used at the user's discretion, depending upon the particular application intended. The opposite end of the wand includes physical and electrical connectors for connection to the sensor probe 3. The wand 66 includes conductors for conducting electrical signals between the controller 39 in the head unit 62 and the sensor probe 3.

Figure 7:
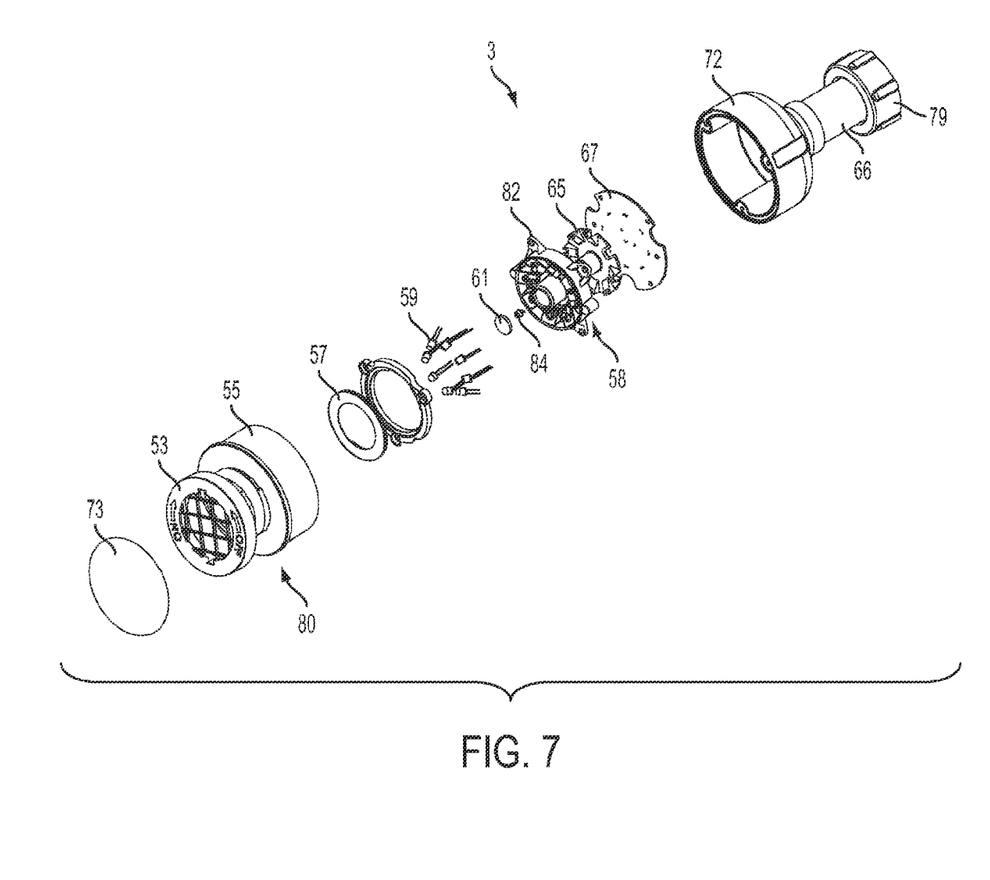
FIG. 7 is an exploded isometric view of a sensor probe used in the handheld moisture sensor device shown in FIG. 1.
Figure 8:
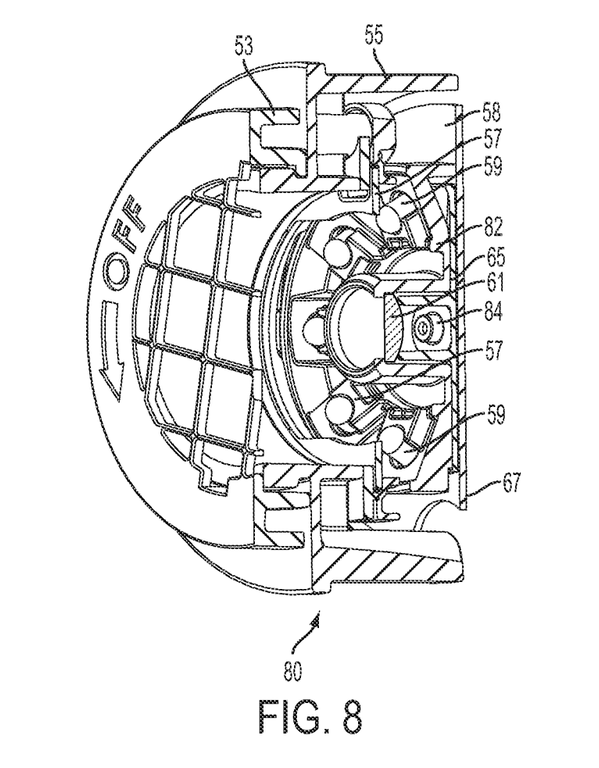
FIG. 8 is a perspective cross sectional view of a portion of the assembled sensor probe of FIG. 7.

FIG. 7 shows detail of the sensor probe 3. As shown there, in this embodiment, the sensor probe 3 includes a housing 72, a lens 61, and a near infrared light source or emitter in the form of an LED array 58. The housing 72 has an end structure 80, including a housing cover 55, adapted to engage material to be examined. The housing 72 further contains the LED array 58 and a near infrared light sensor 84. Sensor 84 is positioned to receive near infrared light reflected off of the material (not shown). The end structure 80 includes a grate 53, which serves to ensure that the biological material is spaced a known distance from the near infrared sensor 84, while at the same time permitting the near infrared light to reach the material. A user of the device 100 thus presses the sensor probe grate 53 against the biological material, so that the material is adjacent, and even in contact with, the grate, but does not pass through the grate. In this embodiment, the grate 53 is connected to the housing cover 55 by a twist-on twist-off connection, but any suitable connection, preferably removable, may be employed.

The LED array 58 includes a base plate in the form of a printed circuit board 67, a mounting plate in the form of an LED clamp 65 mounted to the base plate 67, the LED array 58, with each LED 59 being oriented, by a LED clamping piece 82, at a particular angle for optimum performance, generally slightly toward a central axis of the device 100. The near infrared sensor 84 is located behind the lens 61, along the central axis of the device 100, and the LEDs 59 are spaced apart in a generally concentric pattern about the sensor 84.

The controller 39 includes a way for a user to provide input, in part in the form of the buttons 65, for identifying the material being scanned, among other types of input. In this embodiment, the LEDs 59 in the array 58 are provided in two subsets. The first subset of LEDs 59 emit near infrared light at a wavelength that is minimally absorbing for moisture or water. The second subset of LEDs 59 emit near infrared light at a wavelength that is at or near a peak for absorption by moisture or water. Once the user of the device 100 presses the sensor probe grate 53 against the biological material, as described above, and pulls the trigger 9, the controller 39 causes the first subset of LEDs 59 to emit near infrared light at the first wavelength, the one that is minimally absorbing for moisture or water. This wavelength is used as a reference wavelength. Then the controller causes the second subset of LEDs 59 to emit near infrared light at the second wavelength, the one that is at a peak for moisture or water. The controller 39 determines, based on a comparison of the amounts of reflected near infrared light, the amount of wet material present. With this amount determined, the percent of dry matter is calculated. In the most preferred embodiment, the first wavelength is about 1300 nanometers, and the second wavelength is about 1450 nanometers, but in other embodiments, other wavelengths can be used.

The sensor probe 3 also includes a glass 57 mounted in the housing 72 adjacent the LEDs 59 so that light from the LEDs passes through the glass, the glass being spaced apart from the end structure grate 53 so that the distance between the material, the LEDs and the sensor 84 can be controlled, and so that the material does not touch the glass and affect the reflected light readings. The near infrared light sensor 84 is located on the PCB 67. The lens 61, mounted in the housing 72 adjacent the near infrared sensor 84, causes near infrared light reflected through the glass 57 from the biological material to be focused on the near infrared sensor.

When used throughout this document, the term "glass" is not intended to be limited solely to silicate glass or glass made substantially of silicon dioxide, but rather is intended to include any material that is relatively solid in use and highly transparent, including but not limited to polymeric materials such as polymethyl methacrylate and polycarbonate, including products sold under the trademarks Plexiglass, Lucite and/or Lexan.

Figure 9:
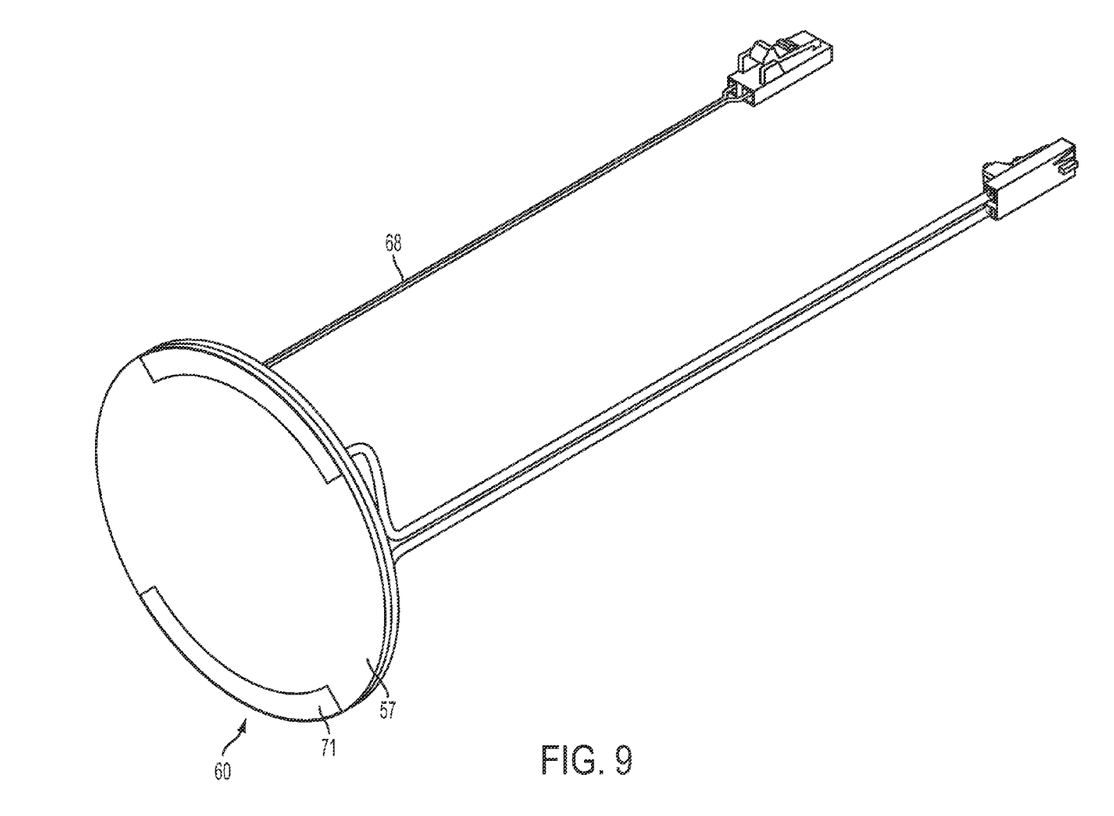
FIG. 9 is a perspective view of a portion of the glass and glass heater in the sensor probe.

As shown in FIG. 7, the device 100 further includes a glass heater 60 adjacent the glass for heating the glass 57. Heating the glass 57 helps to ensure that moisture does not condense on the glass, or to evaporate any moisture that does condense on the glass, as any such condensation could affect the near infrared light readings by the sensor 84. To this end, a glass temperature sensor 68 monitors the temperature of the glass 57 and turns on the glass heater 60 when the glass temperature reading is below a predetermined level, as set in the controller 39. In this embodiment, the glass 57 is coated with a thin layer of ITO. The glass heater 60 includes a pair of contacts 71 on the periphery of the glass 57, positioned opposite one another, with the glass being heated by passing electric current from one contact to the other through the ITO layer.

The device 100 also includes a calibration disc 73 separate from the housing 72, adapted to be positioned near the end structure 80 for use as a known near infrared light reflection material for calibrating the near infrared sensor. When not being used to calibrate the sensor, the calibration disc can be stored remote from the remainder of the device 100. With use and over time, the intensity and other properties of the light emitted by the LEDs 59, and the signal emitted by the sensor 84 based upon a certain amount of light hitting the sensor, can change. Regular calibration of the device 100 based on the LED intensity is therefore advised, to optimize the performance of the device.

The present invention has numerous advantages over the prior art. First, the moisture sensor is handheld and portable, very convenient for the user to use. The moisture sensor is intended to be used nearly anywhere, including at the point of use of the feed, to obtain real time moisture readings. The moisture sensor includes built in forage calibrations, and even permits selection of forage calibration based on the user's particular ingredients by name. It includes preset buttons for quick selection of common ingredients. The moisture sensor has built in reference calibration, which can be further enhanced with field calibrations. The device 100 may also include communication capability, including USB, Wi-Fi to computer, Wi-Fi to scale, and may even include wireless communications (cellular, etc.). The information obtained will allow the user to do auto correction for dry matter in the feeding ration. The batteries in the handle provide good counter balance to the sensor probe at the opposite end of the wand. The invention allows the operator to easily take several readings and average them, which will be less sensitive to inappropriate samples (leaves, stems, large parts or very fine particles).

The design of the probe 3 with the LED NIR (near infrared) array 58 provides for extended battery life and durability over incandescent bulbs. The LEDs 59 are clamped into position for focusing the near infrared light through the glass 57 and onto the material to be measured. As described above, the probe 3 includes a lens 61 to concentrate reflected energy on the near infrared sensor 84. The grate 53 is removable, to accommodate ease of cleaning.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A near infrared spectroscope adapted to be pressed against material to be analyzed, the spectroscope comprising:
    a sensor assembly including a housing with an end structure adapted to engage material to be examined;
    a near infrared light source mounted in the housing;
    a near infrared light sensor mounted in the housing, and positioned to receive near infrared light from the near infrared light source, reflected off of the material;
    a glass mounted in the housing adjacent the light source so that light from the light source passes through the glass, the glass being spaced apart from the end structure, the near infrared light sensor being positioned such that the glass is between the sensor and the end structure;
    a glass heater adjacent the glass and capable of heating the glass; and
    a temperature sensor capable of sensing a temperature from the glass, the glass heater being activated in response to the temperature from the glass being lower than a predetermined value.

2. A near infrared spectroscope in accordance with claim 1 wherein the glass has a periphery, the glass heater including a substantially transparent, conductive, coating, and pair of contacts connected to the coating on the periphery of the glass, each contact positioned opposite the other on the periphery, whereby the glass is heated by passing electric current through the coating from one contact to the other.

3. A near infrared spectroscope in accordance with claim 1 further including a lens mounted in the housing adjacent the near infrared sensor, so that the near infrared light reflected off of the material passes through the glass and is focused on the near infrared sensor by the lens.

4. A near infrared spectroscope in accordance with claim 1 wherein the end structure includes a grate.

5. A near infrared spectroscope in accordance with claim 1 wherein the near infrared light source is a near infrared emitter.

6. A near infrared spectroscope in accordance with claim 5 wherein the spectroscope includes a plurality of near infrared emitters.

7. A near infrared spectroscope in accordance with claim 6 wherein the sensor is located along a central axis of the spectroscope, and the emitters are located substantially concentrically about the sensor.

8. A near infrared spectroscope in accordance with claim 1 wherein the spectroscope further includes a calibration disc separate from the housing, adapted to be positioned near the end structure for use as a near infrared light reflection reference material for calibrating the near infrared sensor.

9. A near infrared spectroscope in accordance with claim 1 wherein the spectroscope further includes a controller connected to the sensor for receiving the reflected near infrared light, the controller including a user input for identifying the material to be scanned.

10. A near infrared spectroscope in accordance with claim 9 wherein the controller determines, based on the amounts of reflected near infrared light, the amount of wet material present.

11. A near infrared spectroscope in accordance with claim 10 wherein a first wavelength of reflected near infrared light is used as a reference wavelength, and a second different wavelength of reflected near infrared light is used to determine the amount of wet material present, taking into consideration the amount of reflected near infrared light of the first wavelength.

12. A near infrared spectroscope in accordance with claim 11 wherein the first wavelength is about 1300 nanometers and the second wavelength is about 1450 nanometers.

13. A near infrared spectroscope adapted to be pressed against biological material to be analyzed, the spectroscope including:

a sensor assembly, the sensor assembly including a housing with an end structure including a grate adapted to engage the material to be examined;

a near infrared LED mounted in the housing;

a near infrared light sensor mounted in the housing and positioned to receive near infrared light from the near infrared LED, reflected off of the material, the sensor being located along a central axis of the spectroscope, and the LED being spaced apart from the sensor;

a glass mounted in the housing adjacent the near infrared LED so that light from the near infrared LED passes through the glass, the glass being spaced apart from the grate and positioned between the grate and the near infrared light sensor;

a glass heater adjacent the glass for heating the glass, the glass heater including a temperature sensor for sensing a temperature from the glass, so that the heater is capable of being activated in response to the temperature from the glass being lower than a predetermined value;

a lens mounted in the housing adjacent the near infrared sensor so that the near infrared light reflected off the biological material passes through the glass and is focused by the lens onto the near infrared sensor; and a controller connected to the near infrared sensor for receiving a signal related to the reflected near infrared light received by the near infrared sensor, the controller including a user input for identifying the material to be scanned, and the controller determining, based on the first amount of reflected near infrared light, the amount of dry material present, and then based on a second amount of reflected near infrared light, the amount of dry and wet material present, with a first wavelength of reflected near infrared light being used to determine the amount of dry material present, and a second different wavelength of reflected near infrared light being used to determine the amount of dry and wet material present.

* * * * *